United States Patent
Sanderson

(10) Patent No.: US 6,906,209 B2
(45) Date of Patent: Jun. 14, 2005

(54) PURIFICATION OF PROPYLENE OXIDE

(75) Inventor: John R. Sanderson, Austin, TX (US)

(73) Assignee: Huntsman International LLC, Salt Lake City, UT (US)

(*) Notice: Subject to any disclaimer, the term of this patent is extended or adjusted under 35 U.S.C. 154(b) by 0 days.

(21) Appl. No.: 10/639,220

(22) Filed: Aug. 12, 2003

(65) Prior Publication Data

US 2004/0082753 A1 Apr. 29, 2004

Related U.S. Application Data

(63) Continuation of application No. PCT/US02/06916, filed on Mar. 6, 2002.
(60) Provisional application No. 60/273,794, filed on Mar. 6, 2001.

(51) Int. Cl.⁷ .................. C07D 301/32; C07D 303/04
(52) U.S. Cl. .................... 549/542; 549/512
(58) Field of Search .................. 549/542, 512; 521/189; 568/679

(56) References Cited

U.S. PATENT DOCUMENTS

| | | |
|---|---|---|
| 4,692,535 A | 9/1987 | Larson et al. |
| 5,235,075 A | 8/1993 | Bachman et al. |
| 5,493,035 A | 2/1996 | Soltani-Ahmadi et al. |

FOREIGN PATENT DOCUMENTS

| | | |
|---|---|---|
| WO | WO 00/55148 | 9/2000 |

*Primary Examiner*—Ba K. Trinh
(74) *Attorney, Agent, or Firm*—Nicole Graham

(57) ABSTRACT

A process for purifying propylene oxide containing an unacceptable quantity of a poly (propylene oxide) polymer contaminant having a number average molecular weight of at least 50,000 and precursors having a number average molecular weight below 50,000. The process comprises contacting the propylene oxide with a sorbent selected from activated carbon, charcoal, and attapulgite for a time and under conditions sufficient to reduce the amount of the contaminant to acceptable levels, and thereafter recovering the purified propylene oxide product, wherein the propylene oxide is contacted with the sorbent at a temperature below 10° C.

3 Claims, No Drawings

PURIFICATION OF PROPYLENE OXIDE

CROSS REFERENCE TO RELATED APPLICATIONS

This application is a continuation of International application PCT/US02/06916, filed Mar. 6, 2002, and claims priority to U.S. Provisional Application Ser. No. 60/273,794, filed Mar. 6, 2001.

FIELD OF THE INVENTION

The present invention relates to processes for the purification of propylene oxide.

BACKGROUND OF THE INVENTION

The present invention relates more particularly to a process of the type described in U.S. Pat. No. 4,692,535 to Larson et al. (hereafter, Larson), wherein a propylene oxide product suitable as an intermediate in the production of polyether polyols for high resilient flexible polyurethane foam applications is made by removing substantially all of a high molecular weight poly(propylene oxide) fraction from an otherwise commercially-acceptable propylene oxide.

As disclosed in the Larson patent, propylene oxide of an otherwise commercially-acceptable purity was found to contain a certain nonvolatile impurity (namely, polypropylene oxide) (or PPO) having a molecular weight of at least 50,000), which impurity made the propylene oxide unsuitable for making polyether polyols to be used with a polyisocyanate and blowing agent in the manufacture of acceptable high resilient flexible polyurethane foams. Polyether polyols prepared from propylene oxide having in excess of 0.1 parts per million by weight of the high molecular weight poly(propylene oxide) impurity were determined to lead to low foam rise and substantial blow hole formation in the polyurethane foams, whereas polyether polyols made from propylene oxide having reduced levels of the high molecular weight PPO impurity produced polyurethane foams with high good foam rise and without substantial blow hole formation.

The solution proposed by Larson involved filtering or percolating either crude liquid propylene oxide of 95 percent or greater propylene oxide content or propylene oxide of otherwise commercially-acceptable, 99 percent purity or better through a fixed bed of an adsorbent material at a temperature ranging from between 10° C. and 100° C. The sorbent materials suggested by Larson as suitable for this purpose are activated carbon, charcoal and attapulgite, and granular forms are said to be preferable to powdered forms of these materials. The quantities of sorbent to be used per unit volume of propylene oxide to be treated are estimated at from about 0.001 to about 0.01 grams or more of solid sorbent per gram of propylene oxide, with contact times ranging from about 1 to about 15 minutes, temperatures of from about 10 to about 100° C., and pressures ranging from atmospheric to superatmospheric.

There are various difficulties associated with the treatment of propylene oxide with activated carbon. Due to the considerable heat released upon sorption of propylene oxide on activated carbon, there are both hazards and possible damage to the carbon bed associated with excessive temperature increases during the initial or start-up phase of the activated carbon treatment process. Where the bed is contacted with liquid propylene oxide, the accompanying sorption exotherm has resulted in propylene oxide vaporization and migration in the bed which in turn causes secondary exotherms with temperatures in excess of 500° C. with extreme hazard and reactor damage. During bed changeover, a major concern has been the handling of toxic and hazardous carbon/propylene oxide/water slurries, which pose safety and environmental hazards.

Prior carbon treatment procedures have required vapour recovery systems, the provisions of steam, nitrogen, cooling, flare facilities as well as sophisticated control systems and trained operators.

Difficulties are compounded by the fact that high molecular weight poly (propylene oxide) polymer can be formed during shipping and storage of propylene oxide and this polymer formation has a pronounced adverse effect on the use of polyols formed from the propylene oxide in polyurethane foams.

SUMMARY OF THE INVENTION

Surprisingly, it was found that the sorbent materials referred to above may be used advantageously in the purification of propylene oxide, provided the treatment with the sorbent material is conducted at temperatures below 10° C., preferably between 8° C. and −40° C., and most preferably between 5° C. and −20° C. Evidently the lowest temperature achievable is about −112° C. meaning the freezing point of the PO.

It has been found that the temperature range referred to above increases the filtration and/or sorption efficiency of the sorbent material/process. It is believed that the lower temperature tends to promote the sorption and/or filtration capacity of said materials. While the underlying phenomena are not fully understood, it appears that there are temperature depending filtration and/or sorption effects involved in the removal of PPOs from PO. In particular it is believed that in fact the lower number average molecular weight PPOs (<50,000) are more readily filtered and or sorbed. Said lower molecular weight PPOs act as precursors to formation of the PPOs having a number average molecular weight of at least 50,000 so that their removal improves the long-term storage quality of the PO. In addition, it has been found that the purification method according to the present invention is advantageously used shortly, preferably within a week, before the manufacturing of the polyol takes place. In case the PO needs to be shipped and/or stored then this should be preferably done under good storage conditions such as stainless steel containers.

"Sorption" in the context of the present invention does include absorption as well as adsorption. Adsorption refers to the collecting of molecules by the external surface or internal surface (walls of capillaries or crevices) of solids or by the surface of liquids. Absorption refers to processes in which a substance penetrates into the actual interior of crystals, of blocks of amorphous solids or of liquids.

DETAILED DESCRIPTION OF THE INVENTION

The present invention is directed to a process for purifying propylene oxide containing an unacceptable quantity of a poly (propylene oxide) polymer contaminant having a number average molecular weight of at least 50,000 and precursors having a number average molecular weight below 50,000. The process comprises contacting the propylene oxide with a sorbent selected from activated carbon, charcoal and attapulgite for a time and under conditions sufficient to reduce the amount of said contaminant to acceptable levels, and thereafter recovering the purified propylene oxide product, wherein the propylene oxide is contacted with said sorbent at a temperature below 10° C., preferably between 8° C. and −40° C., and most preferably between 5° C. and −20° C. "Unacceptable" and "acceptable" in this context refer to those levels of the poly(propylene oxide) contaminant which make the polyether polyols produced from propylene oxide containing such levels of such contaminant commercially unacceptable or acceptable, respectively, for making high resilient flexible polyurethane foams.

In another, related aspect, the invention provides a process for making polyether polyols from propylene oxide, wherein the propylene oxide has been purified according to the process described in the preceding paragraph. In still another aspect, a process for making high resilient flexible polyurethane foams from the just-mentioned polyether polyols is provided.

The treatment with the sorbent is conducted at temperatures below 10° C., preferably between 8° C. and −40° C., and most preferably between 5° C. and −20° C.

In general, the purification process of the present invention is effected in conventional manner by employing the static-bed percolation process, which is a cyclic process wherein the propylene oxide to be refined is passed through a stationary bed of granular sorbent under controlled conditions. Propylene oxide subjection to the purification process is continued until the product propylene oxide has attained the desired specification with respect to poly (propylene oxide) contaminant content. The use of atmospheric or superatmospheric pressure operations in carrying out the process of this invention is a matter of choice depending upon the relative economics, taking into account the apparatus design and cost. Moreover, the pressure at which the process is carried out has no effect on the concept of the present purification process. Preferred temperatures of treatment reside between 5° C. and −20° C. Preferably the pressure is atmospheric or the pressure employed can be higher than atmospheric.

In general, solid sorbents, for example, activated carbon, when employed to decolorize solutions, are simply slurried with the solution and then removed as, for example, by filtration. Such sorbents have also been employed by percolating the solution to be decolorized throughout a bed of the solid sorbent. For such general decolorizing uses, either method of contacting the solution with the sorbent has been deemed as equivalent, because substantially the same results are said to be obtained. However, in the method of the present invention, the method of contacting the propylene oxide liquid with the solid sorbent is important, for more than decolorizing is accomplished. Hence, in the purification of propylene oxide of high purity by the method of this invention, contacting of the propylene oxide with a bed of solid sorbent, for example activated carbon, results in a more selective sorption and/or filtration in the form of the afore-characterized low and high molecular weight poly (propylene oxide).

The quantity of solid sorbent employed per unit volume of propylene oxide to be treated will vary not only with the efficiency of the solid sorbent to absorb impurities, but also with the amount of impurities present at the time of contact. In general, the adsorptive capacity life of the solid sorbent is limited by the adsorptive capacity for the poly(propylene oxide) contaminant, and not any impurities (e.g. color bodies) that may be present in the propylene oxide liquid itself. Typically, the contact time will be in the range from 1 to about 120 minutes so as to provide sufficient solid sorbent treatment to attain the objectives of the method of this invention.

As indicated above, not all solid sorbents are suitable for use in the practice of the purification process of the present invention. Exceptionally useful activated carbons or charcoals include those obtained from lignite, gas black, coconut, bagasse, wood, sawdust, pulp-mill waste, blood, bone, etc. Specific activated carbons include Calgon Corporation granular carbons, NORIT granular activated carbons, Cenco activated carbons, products of Central Scientific Company, Nuchar activated carbons, products of West Virginia Pulp and Paper Company, and products of Darco Division, ICI AMERICAS, Inc. Illustrative commercially available carbons include Type CAL granular carbon (Calgon Corporation) and NORIT RO.8 granular activated carbon (NORIT Corporation). Attapulgite sorbents employable in the purification process of the present invention are available from Engelhard Minerals and Chemicals Corporation. The grades of Attapulgus Clay normally recommended for contact purification are 100/UP Mesh RVM and 200/UP Mesh RVM. The finer grade 200/UP RVM is normally used unless higher rates of filtration are required, in which case 100/UP RVM is used. In the case of purification by percolation, a sorbent bed usually consisting of carbon is preferred and the liquid is allowed to flow downward at controlled temperature and contact time. It is preferred to use the solid sorbent (i.e. activated carbon, charcoal or attapulgite) in a granular form rather than a powdered form.

Sorption of the high molecular weight poly (propylene oxide) impurity from liquid propylene oxide has been found to be determined, in conventional manner, by the type of concentration profile in the sorbent bed column (feed rate and impurity concentration of feed being constant) at any interval of time. This concentration profile is a planar front and therefore the sorption is chromatographic in nature. Hence, the solution upstream of the planar front contains the feed concentration of the poly(propylene oxide) impurity and the propylene oxide liquid downstream of the planar front contains reduced poly (propylene oxide) impurity. From this established fact of planar front sorption, the theoretical performance of a column of various sorbents, such as activated carbons, can readily be determined from sorption isotherm determinations. It is appreciated that the adsorptive characteristics of a sorbent vary from type of sorbent to type of sorbent. Even particle size contributes to the variances. But, by the well known sorption isotherm determination coupled with the established planar front sorption of poly(propylene oxide) purity, only simple routine tests are required to determine the performance of the column of any specific sorbent. It is clear from the foregoing that a precise ratio or range of sorbent to poly(propylene oxide) impurity or crude propylene oxide can not be given because to do so would require testing all known sorbents which are subject to change by their manufacturer. According to another embodiment of the present invention, it has been found that the higher molecular weight PPO collect at the top of the column. The PPO can be easily removed by backwashing of the column and therefore reduced the frequency at which the bed needs to be replaced.

Those skilled in the art will appreciate, however, that the optimum parameters of operation for any given stationary bed arrangement will depend on, for example, the carbon employed and on the degree of purification required, but it is considered that these persons will be well able to select those parameters given the present disclosure.

After the propylene oxide has been purified by passing it through the carbon bed, the propylene oxide may be further treated.

Carbon bed experiments were done using Norit carbon at the temperatures claimed demonstrating superior removal of low molecular weight PPO by the carbon treater.

What is claimed:

1. A process for purifying propylene oxide from a propylene oxide composition containing poly (propylene oxide) polymer contaminents having a number average molecular weight of at least 50,000 and precursors having a number average molecular weight below 50,000 comprising the steps of:

(a) contacting the propylene oxide composition with a sorbent selected from the group consisting of activated carbon, charcoal, and attapulgite at a temperature below 10° C. for a time and under conditions sufficient to reduce the amount of the contaminant to acceptable levels, and (b) recovering purified propylene oxide product.

2. The process according to claim 1 wherein the propylene oxide is contacted with the sorbent at a temperature between 8° C. and −40° C.

3. The process according to claim 1 wherein the propylene oxide is contacted with the sorbent at a temperature between 5° C. and −20° C.

* * * * *